United States Patent
Fischer et al.

(10) Patent No.: US 8,979,836 B2
(45) Date of Patent: Mar. 17, 2015

(54) ENDOSCOPIC SURGICAL INSTRUMENT

(75) Inventors: Klaus Fischer, Nagold (DE); Jochen Queck, Tübingen (DE); Friedrich Kalthoff, Meinerzhagen (DE)

(73) Assignee: Erbe Elektromedizin GmbH, Tuebingen (DE)

( * ) Notice: Subject to any disclaimer, the term of this patent is extended or adjusted under 35 U.S.C. 154(b) by 1402 days.

(21) Appl. No.: 11/918,251

(22) PCT Filed: Mar. 14, 2006

(86) PCT No.: PCT/EP2006/002328
§ 371 (c)(1),
(2), (4) Date: Oct. 11, 2007

(87) PCT Pub. No.: WO2006/108480
PCT Pub. Date: Oct. 19, 2006

(65) Prior Publication Data
US 2009/0069805 A1    Mar. 12, 2009

(30) Foreign Application Priority Data

Apr. 11, 2005 (DE) .................. 10 2005 016 602
May 4, 2005 (DE) .................. 10 2005 020 948
Aug. 16, 2005 (DE) .................. 10 2005 038 694

(51) Int. Cl.
| | | |
|---|---|---|
| A61B 18/18 | (2006.01) |
| A61B 17/3205 | (2006.01) |
| A61B 17/3203 | (2006.01) |
| A61B 17/34 | (2006.01) |
| A61B 18/14 | (2006.01) |
| A61B 17/00 | (2006.01) |
| A61B 17/22 | (2006.01) |

(52) U.S. Cl.
CPC ....... *A61B 17/32056* (2013.01); *A61B 17/3203* (2013.01); *A61B 17/3478* (2013.01); *A61B 18/1482* (2013.01); *A61B 2017/00269* (2013.01); *A61B 2017/22074* (2013.01); *A61B 2018/1407* (2013.01)
USPC .......................................................... 606/41

(58) Field of Classification Search
USPC ................................. 606/40–45, 167; 604/22
See application file for complete search history.

(56) References Cited

U.S. PATENT DOCUMENTS

| | | | |
|---|---|---|---|
| 5,116,313 A | | 5/1992 | McGregor |
| 5,158,561 A | * | 10/1992 | Rydell et al. ................... 606/113 |
| 5,505,729 A | | 4/1996 | Rau et al. |
| 5,738,677 A | * | 4/1998 | Colvard et al. ................... 606/4 |
| 5,741,271 A | * | 4/1998 | Nakao et al. ................... 606/114 |
| 6,010,512 A | | 1/2000 | Chu et al. |
| 6,123,665 A | * | 9/2000 | Kawano ........................ 600/104 |

(Continued)

FOREIGN PATENT DOCUMENTS

| | | |
|---|---|---|
| DE | 2 333 720 | 1/1975 |
| DE | 36 42 077 | 6/1988 |

(Continued)

*Primary Examiner* — Joseph Stoklosa
*Assistant Examiner* — Amanda Scott
(74) *Attorney, Agent, or Firm* — Dickstein Shapiro LLP

(57) ABSTRACT

The application relates to an endoscopic surgical instrument, and in particular to an instrument for endoscopic mucosa resection. The instrument includes a device for feeding in at least one liquid (for injection and/or dissection) and a device for high frequency surgery. These devices are combined within a single surgical instrument, in the interest of uniform handling.

21 Claims, 4 Drawing Sheets

(56) References Cited

U.S. PATENT DOCUMENTS

| | | | |
|---|---|---|---|
| 6,527,753 B2 * | 3/2003 | Sekine et al. | 604/264 |
| 6,689,126 B1 | 2/2004 | Farley et al. | |
| 7,118,566 B2 * | 10/2006 | Jahns | 606/41 |
| 2003/0009166 A1 | 1/2003 | Moutafis et al. | |
| 2003/0216724 A1 * | 11/2003 | Jahns | 606/41 |
| 2003/0233090 A1 | 12/2003 | Whayne | |

FOREIGN PATENT DOCUMENTS

| | | |
|---|---|---|
| DE | 42 42 143 | 6/1994 |
| DE | 196 07 922 | 1/1998 |
| DE | 100 28 413 A1 | 9/2001 |
| EP | 0 280 972 A1 | 2/1988 |
| EP | 0 280 972 A1 | 9/1988 |
| EP | 0 555 549 A1 | 12/1992 |
| EP | 0 893 101 A2 | 1/1999 |
| JP | 05-212045 | 8/1993 |
| JP | 11-47154 A | 2/1999 |
| JP | 2000-262528 A | 9/2000 |
| JP | 2004-105367 A | 4/2004 |
| WO | WO 96/36381 | 11/1996 |
| WO | WO 03/096871 A2 | 11/2003 |

* cited by examiner

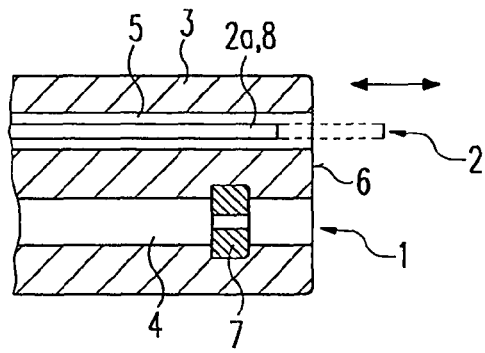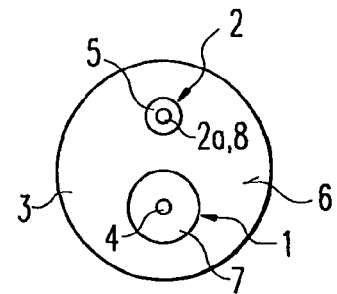
Fig. 1a  Fig. 1b
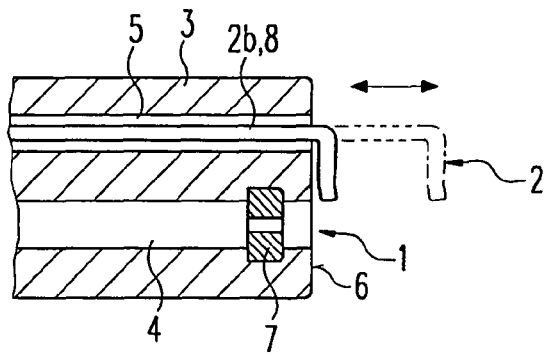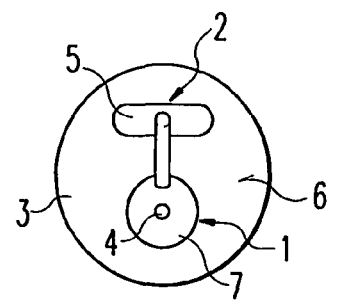
Fig. 2a  Fig. 2b
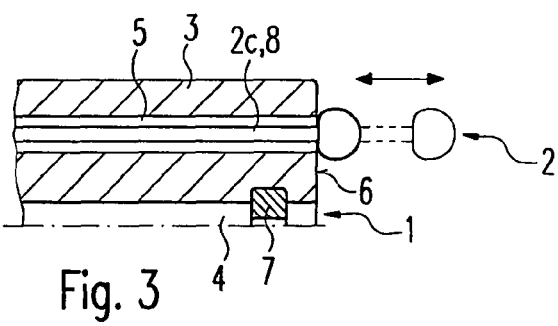
Fig. 3
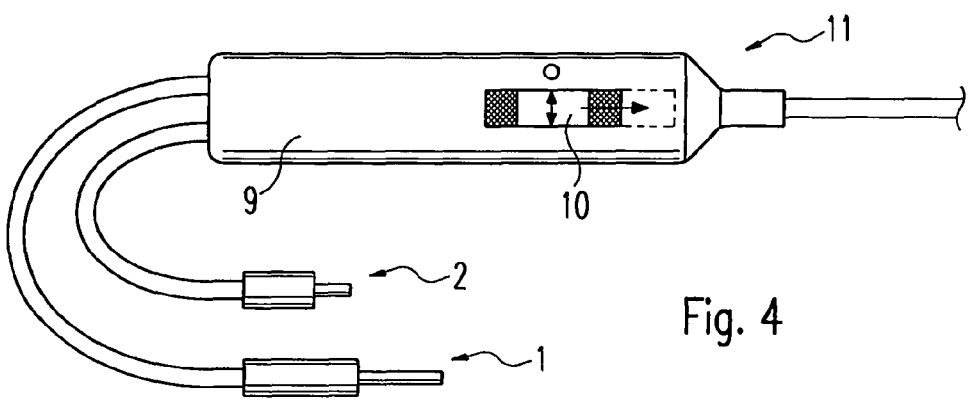
Fig. 4

ENDOSCOPIC SURGICAL INSTRUMENT

FIELD OF THE INVENTION

The invention relates to an endoscopic surgical instrument, and in particular to an instrument for endoscopic mucosa resection.

BACKGROUND OF THE INVENTION

The resection of large area turnouts in the gastrointestinal tract which are restricted to the mucosa should be carried out in one session and the tumours must be as fully excised as possible. Conventionally, the snare technique or the cap technique is used to achieve these goals, however, with these techniques, varying sizes of circular operative specimens can only be produced by varying the snare diameter or the cap diameter. Therefore, large area turnouts with a diameter of more than 8 cm can only be removed using a piecemeal technique. However, complete excision of large area turnouts is desired. To this end, some first methods have been used wherein the mucosa has been cut into a round, piece-by-piece, with a flexible needle and then completely removed. In this process, the resection must take place in the submucosa. The layer thicknesses are approximately 0.5 mm to 1.5 mm.

During endoscopic mucosa resection, bleeding and perforation of the intestinal or gastric wall can occur. In order to tackle these problems, liquid is injected under the mucosa with a flexible needle before the resection. The needle must be precisely placed within the submucosa. The penetration of the liquid into the mucosa causes the mucosa to be loosened from the Muscularis propria and forms a liquid cushion forms beneath the mucosa. This produces a safety separation from the Muscularis propria as well as a heat barrier. The mucosa resection is then carried out with a flexible needle knife. A suitable device for endoscopic injection of a liquid underneath the mucosa is described, for example, in DE 19 607 922 C2.

This technique for resection is extremely difficult and the operation duration for interventions of this type is currently between 2 and 6 hours. In particular, the difficulty of this type of intervention is that the injected liquid slowly leaks out of the submucosa during the operation, causing the Muscularis propria to become thermally damaged by the needle. This thermal damage can in turn lead to perforation of the intestine. In order to avoid this perforation, the instrument must be removed several times during the resection procedure and liquid must again be injected under the mucosa.

Alternative solutions to the problems of bleeding and intestinal perforation are being tested wherein liquids of different viscosity are used which leak out of the mucosa more slowly. However, these attempts still do not offer a satisfactory solution because the escape of the liquid out of the submucosa is only slowed, but not prevented.

It is therefore an object of the invention to provide a surgical instrument which may to facilitate endoscopic interventions, such as mucosa resection, wherein damage to the surrounding tissues, particularly the intestinal or gastric wall, may be reliably avoided.

BRIEF DESCRIPTION OF THE DRAWINGS

The following describes the invention with reference to examples of embodiments which are described in more detail with reference to the following figures:

FIG. 1a is a longitudinal cross-sectional view of the distal end of a probe with a high frequency needle, according to an exemplary embodiment of the invention.

FIG. 1b is a transverse cross-sectional view of the probe of FIG. 1a.

FIG. 2a is a longitudinal cross-sectional view of the distal end of a probe with a high frequency hook, according to an exemplary embodiment of the invention.

FIG. 2b is a transverse cross-sectional view of the probe of FIG. 2a.

FIG. 3 is a longitudinal cross-sectional view of the distal end of a probe with a high frequency needle with an insulated tip, according to an exemplary embodiment of the invention.

FIG. 4 is a side view of a handle including a liquid connection and a high frequency connection.

DETAILED DESCRIPTION OF THE INVENTION

Figure 5:
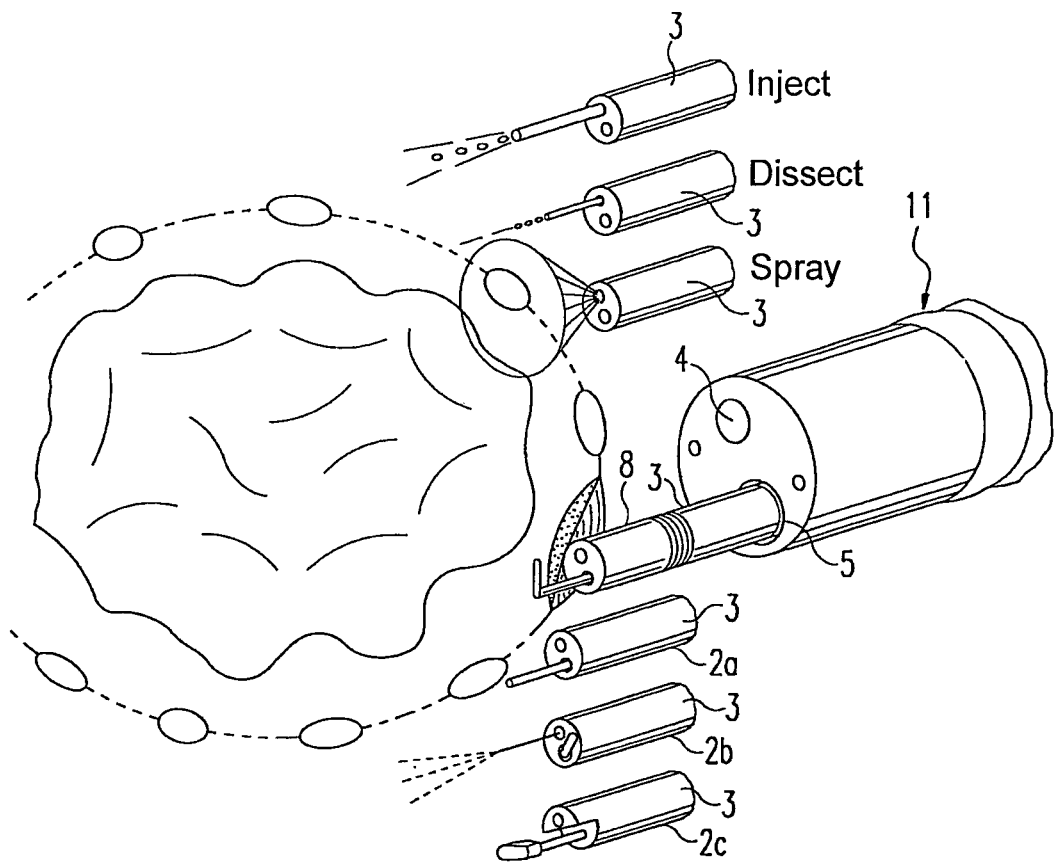
FIG. 5 is a diagram showing the sequence of an endoscopic intervention using a surgical instrument according to the invention.
Figure 6:
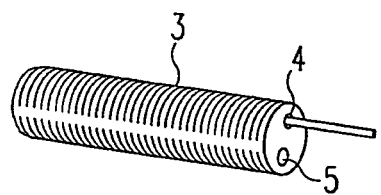
FIG. 6 is a perspective view of an exemplary embodiment of the invention, wherein the device is operated in an injection mode.
Figure 7:
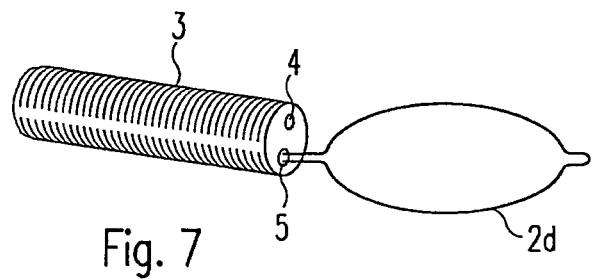
FIG. 7 is a perspective view of an exemplary embodiment of the invention, wherein the device is operated in a high frequency mode.
Figure 8:
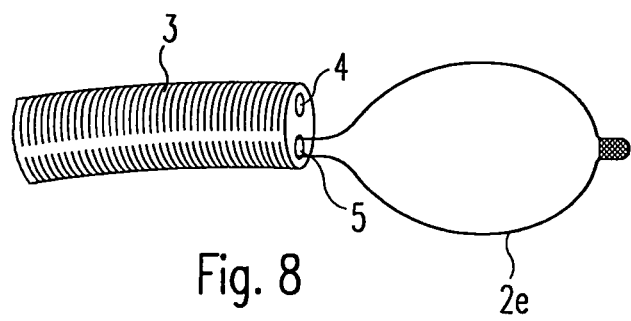
FIG. 8 is a perspective view of an exemplary embodiment of the invention, wherein the probe includes a high frequency snare with an insulated tip.

The invention provides an endoscopic surgical instrument that includes a device for feeding in at least one liquid, in particular for injection and/or dissection, and a device for high frequency surgery, wherein the device for high frequency surgery is combined with the device for feeding in the at least one liquid, in order to achieve uniform handling.

A multifunction device is thereby achieved, which combines the advantages of water jet surgery (including injection of the liquid and/or dissection by means of liquid) with the advantages of high frequency surgery. The surgical instrument according to the invention makes it possible to inject liquid under the mucosa with the water jet in a dosed manner and thereby to lift it away from the Muscularis. Furthermore, the mucosa can also be cut by the water jet when operated at a suitable pressure, so that two functions can be fulfilled by the surgical instrument according to the invention; specifically injection of the liquid into the submucosa and resection of the mucosa.

In order to separate the submucosa, the device for high frequency surgery is used. With the aid of the surgical instrument according to the invention, it is also possible to perform resection of the mucosa with the device for high frequency surgery rather than with the aid of the liquid. In this case, the device for feeding in the at least one liquid is used only for injection of fluid for lifting the mucosa.

One advantage of the surgical instrument according to the invention is that the functions of injecting liquid under the mucosa, separation of the mucosa and separation of the submucosa can be carried out with the aid of a single device. Therefore, changing of instruments during the operation is no longer required. Rather, when using the endoscopic surgical instrument according to the invention, when the liquid leaks out of the submucosa, the device is simply switched over from cutting mode to injection mode and additional liquid in injected in the submucosa. Operating times can therefore be significantly reduced because the instruments do not have to be removed.

Preferably, the device for feeding in the at least one liquid has a flexible probe with at least two working channels. A nozzle is arranged in one of the working channels and a high frequency electrode is arranged in another of the working channels, each in the region of the distal end of the probe. This arrangement of the nozzle and the high frequency electrode in two working channels of one probe offers a solution for combining the device for feeding in the at least one liquid (e.g., nozzle) and the device for high frequency surgery (e.g., high frequency electrode) for uniform handling.

The device for high frequency surgery may comprise a needle, a hook, a needle with an insulated tip, a disk, a snare or a snare with an insulated tip, by which means the field of application of the device is widened. The design of a high frequency device as a snare with or without an insulated tip is particularly suitable for polypectomy. It has previously been problematic that under certain circumstances the polyp was not sufficiently spaced from the mucosa and could not be lifted off. The cutting height, therefore, was a matter of judgement for the surgeon. The surgeon was required to balance between removing a sufficient amount of the polyp such that no risky material (which later could degenerate) is left in the body and maintaining a sufficient distance from the submucosa so as to not endanger the tissue of the intestinal wall (i.e. risk of perforation).

The combination of a high frequency snare and a device for feeding in a liquid, as in the invention, enables the injection of a liquid jet under the polyp, so that it is sufficiently spaced from the submucosa. The polyp can then be excised or resected without risk that the tissue of the intestinal wall will be damaged. Any type of snare, i.e. symmetrical or asymmetric snares, snares with or without insulated tips, snares with different shapes or diameters, can be used.

In a preferred embodiment, the surgical instrument comprises a handle which also has a switch, in particular a sliding switch, for switching on the device for high frequency surgery and a separate switch, in particular a foot switch, for activating the device for high frequency surgery. Two spatially separate switches must thereby be actuated, so that the device for high frequency surgery is switched on by the sliding switch and then activated by actuating the separate foot switch. It is thereby ensured that the device for high frequency surgery is not accidentally activated.

The separate foot switch can be adapted both for activating the device for high frequency surgery and for activating the feeding-in of the at least one liquid, so that by means of the separate foot switch both the feeding-in of the liquid and the activation of the high frequency electrode can be actuated.

The probe can be comprised of a plastic hose, which results in a particularly simple and economical solution for flexibly designing the probe. Alternatively, the probe can be comprised of a flexible metal tube, which is insulated on the outer periphery. By means of the metal inner core, the probe diameter can be significantly reduced without a severe loss of flexibility.

FIGS. 1a and 1b show the distal end 6 of a probe 3 according to an exemplary embodiment of the endoscopic surgical instrument or endoscope 11 of the invention. The probe 3 has two working channels 4, 5. A nozzle 7 is firmly arranged in one of the working channels 4. At least one liquid, in particular a NaCl solution, can be fed through this working channel 4. The working channel 4 is therefore part of the device 1 for feeding in at least one liquid. This device 1 also comprises a supply container for the liquid and a pump arrangement through which the liquid is forced through the working channel 4 under pressure.

Figure 10:
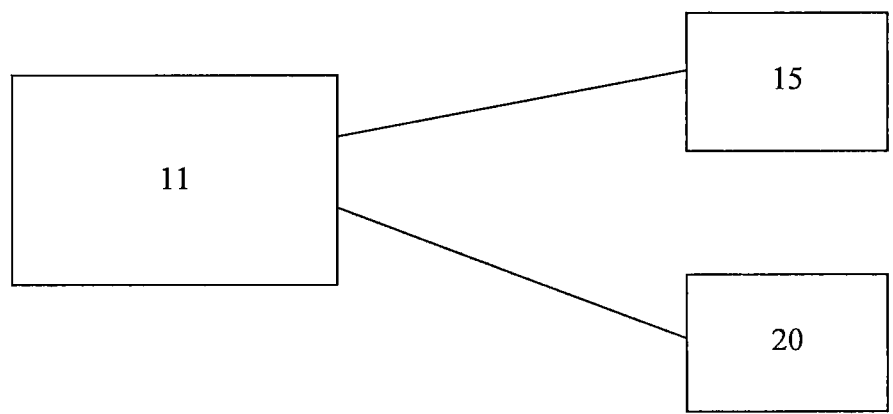
FIG. 10 is a schematic block diagram of an exemplary embodiment of the invention.

Furthermore, the device 1 for feeding in the at least one liquid, i.e. the device for water jet surgery, can be switched from the injection mode to the dissection mode, and vice versa, by a suitable pressure control system, such as pressure regulator 20 (FIG. 10). In the injection mode, the device 1 functions as a needle-free injector according to the principles known from DE 2 333 720 A1 and U.S. Pat. No. 5,116,313.

Also provided in the probe 3 is a device 2 for high frequency surgery. This device 2 for high frequency surgery comprises a high frequency electrode 8, which is provided in the other working channel 5 in the probe 3. The two working channels 4, 5 are arranged substantially parallel to one another. It should be noted that the invention is not restricted to two working channels and can comprise additional working channels, in particular three or four working channels, wherein different functions can be assigned to each of the different working channels. For example, two separate working channels could be provided for the injection mode and the dissection mode, in addition to the working channel provided for the high frequency electrode 8. By this means, an injector provided with a needle, the water jet nozzle 7 and the high frequency electrode 8 could be controlled via three separate working channels.

Devices for optical monitoring of the intervention, such as light guides (not shown), are also provided in the endoscope 11.

Depending on the field of application, the high frequency electrode 8 may comprise a high frequency needle 2a (FIG. 1a), a high frequency hook 2b or spatula (FIG. 2a) arranged in twist-proof manner, a high frequency needle with insulated tip 2c, in particular a ceramic tip (FIG. 3) or a disk (not shown).

The endoscope 11 also comprises a handle 9, shown in FIG. 4. The handle 9 has a connection for the device 2 for high frequency surgery, which can be connected to a high frequency unit (not shown). The handle 9 also has at least one liquid connection of the device 1 for feeding in the at least one liquid, which can be linked to a water jet surgery unit (not shown). The two connection lines are fed through the handle 9 and into the endoscope 11.

The handle 9 also has a switch 10, in particular a sliding switch, the actuation of which allows the high frequency electrode 8 to be positioned and switched on. For positioning, the high frequency electrode 8 is moved out of the probe 3, as indicated by the double arrow and the dotted representation of the electrode 8 in FIGS. 1a, 2a and 3. Activation of the high frequency electrode 8 is carried out with a foot switch 15 (FIG. 10), by which means unintentional actuation of the electrode 8 is reliably avoided. Activation of the water jet can be carried out with the same foot switch 15.

The surgical instrument or endoscope 11 according to the invention is used as follows. As shown in FIG. 5, the water jet surgery function of the surgical instrument is activated and a fine injection jet is created using the working channel 4 and the nozzle of the probe 3, so that a liquid and particularly a NaCl solution is injected under the mucosa into the submucosa. This forms a liquid cushion under the mucosa so that the mucosa is lifted off the Muscularis propria. In the next step, the surgical instrument is switched from injection mode to dissection mode, wherein the pressure of the water jet is increased so that the mucosa can be resected. If necessary, liquid can be sprayed onto the operation area through the working channel 4, i.e. within the context of the water jet surgical function of the endoscope 11 according to the invention.

The instrument is then switched from the water jet function to the high frequency surgical function and the electrode 8 is positioned. By activating the high frequency electrode 8, the submucosa is separated, during which the coagulating effect of the electrode 8 comes into play.

Accordingly, it is possible to lift the mucosa sufficiently off the Muscularis propria and to excise it without the gastric or intestinal wall being damaged, while using only a single instrument. Specifically, it is possible to reinject liquid into the submucosa if the submucosa loses too much liquid during the course of the operation, without changing devices, in order to keep the mucosa adequately spaced from the gastric or intestinal wall.

The probe 3 is flexibly designed, for example as a plastic hose or as a flexible metal tube which is externally insulated by a plastic hose.

A further preferred exemplary embodiment of the invention is shown in FIGS. 6 to 9. This exemplary embodiment is particularly suited to polypectomy and comprises a probe 3 with two working channels 4, 5, of which one working channel 4 serves for the injection of a liquid jet and the other working channel 5 serves to accommodate a high frequency snare. The two working channels are integrated into one probe 3 for uniform operation. The uniform operation of the injection device and the cutting device can be achieved with the exemplary embodiment according to FIGS. 6 to 9, just as with all the other exemplary embodiments, in that two separate hoses each with one working channel 4, 5 are connected to one probe.

Figure 9:
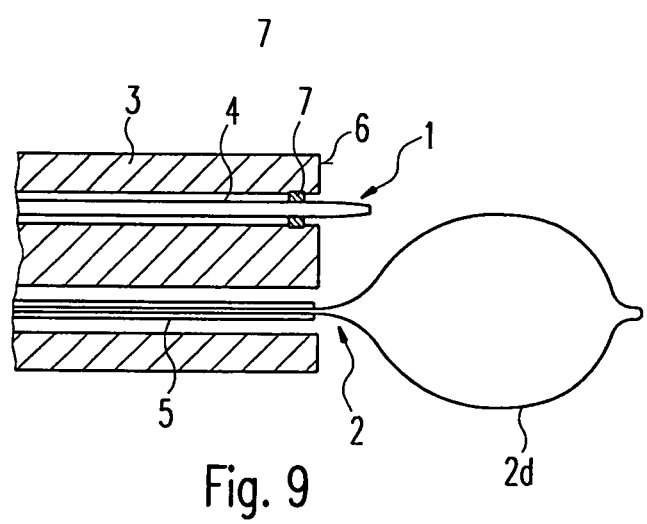
FIG. 9 is a longitudinal cross-sectional view of a probe with a high frequency snare without an insulated tip, according to an exemplary embodiment of the invention.

The design of the probe according to FIG. 9 substantially corresponds to the above described design of the probe according to the previously described exemplary embodiments. A nozzle 7, through which the liquid jet for injection or dissection emerges, is arranged in one of the two working channels 4. A high frequency snare is arranged in the other of the two working channels 5 and can be drawn into or pushed out of the working channel 5. All types of snare in different forms and diameters and snares 2e with an insulated tip (FIG. 8) and snares 2d without an insulated tip (FIG. 9) are suitable. Furthermore, symmetrical or asymmetric and/or rotatable or non-rotatable snares can be used.

The functioning of the probes 3 according to the exemplary embodiments as per FIGS. 6 to 9 substantially corresponds to the functioning of the exemplary embodiments described above, wherein, in the injection mode, a liquid jet, preferably 0.9% NaCl solution, is injected into the submucosa under the polyps, so that it is sufficiently spaced from the submucosa. The polyp is then resected or excised by means of the snare 2d, 2e.

The invention claimed is:

1. A surgical instrument comprising:
a device for feeding in at least one liquid, the device for feeding in the at least one liquid being configured such that needleless injection of and/or dissection with the at least one liquid occurs; and
a device for high frequency surgery, wherein the device for high frequency surgery is combined with the device for feeding in the at least one liquid,
wherein the surgical instrument is an endoscopic surgical instrument for endoscopic mucosa resection, and
wherein the at least one liquid has a first pressure during needleless injection and a second different pressure during resection.

2. The surgical instrument according to claim 1, further comprising:
a flexible probe which comprises two working channels,
wherein the device for feeding in the at least one liquid comprises a nozzle-arranged in one of the working channels at distal end of the probe; and
wherein the device for high frequency surgery comprises a high frequency electrode arranged in another of the working channels at the distal end of the probe.

3. The surgical instrument according to claim 2, wherein the probe comprises a plastic hose.

4. The surgical instrument according to claim 2, wherein the probe comprises a flexible metal tube which is insulated on its outer periphery.

5. The surgical instrument according to claim 1, wherein the device for high frequency surgery comprises one of the group consisting of a needle, a hook, a needle with an insulated tip, a disk, a snare and a snare with an insulated tip.

6. The surgical instrument according to claim 1, further comprising:
a handle, the handle comprising:
a sliding switch for switching on the device for high frequency surgery; and
a foot switch, for activating the device for high frequency surgery.

7. The surgical instrument according to claim 6, wherein the foot switch is adapted both for activating the device for high frequency surgery and for activating the device for feeding in the at least one liquid.

8. A surgical instrument, comprising:
a device configured to guide at least one fluid through a first channel to allow at least one process selected from the group consisting of needleless injection, resection, and dissection of tissue to occur; and
a high-frequency electrode positioned within a second channel,
wherein the surgical instrument is an endoscopic surgical instrument, and
wherein the fluid has a first pressure during needleless injection and a second different pressure during resection.

9. The surgical instrument of claim 8, wherein the device guides the at least one fluid to conduct needleless injection, resection, and dissection of tissue.

10. The surgical instrument of claim 8, wherein the high-frequency electrode is selected from the group consisting of a needle, a hook, a disc, and a snare.

11. A surgical instrument, comprising:
a tube with a plurality of channels;
a nozzle located in one of the plurality of channels for allowing a fluid to pass therethrough, the one of the plurality of channels being in communication with a pressure regulator, the pressure regulator causing the fluid to flow through the one of the channels at different pressures, wherein, at a first pressure, the instrument functions in a needleless injection mode, and wherein, at a second pressure, the instrument functions in a resection mode; and
a high frequency device located in another one of the plurality of channels,
wherein the surgical instrument is an endoscopic surgical instrument.

12. The surgical instrument of claim 11, wherein the fluid is water or saline solution.

13. The surgical instrument of claim 11, wherein the second pressure is higher than the first pressure.

14. A method of surgery, comprising the steps of:
providing an endoscopic instrument at a site in the vicinity of anatomical tissue;
operating the endoscopic instrument in a needleless injection mode to allow a fluid to be injected in the anatomical tissue at a first pressure; and
operating the endoscopic instrument in a cutting mode to allow a portion of the anatomical tissue to be removed,
wherein the steps of operating the endoscopic instrument in an injection mode and in a cutting mode are conducted without removing the endoscopic instrument from the site.

15. The method of claim 14, wherein the anatomical tissue is removed by the fluid at a second pressure which is greater than the first pressure.

16. The method of claim 14, wherein the anatomical tissue is removed by operating a high-frequency device located within one of a plurality of channels of the endoscopic instrument.

17. The method of claim 16, wherein the high-frequency device is located in a channel different from a fluid injection channel.

18. A method of endoscopic removal of biological tissue comprising a mucosal layer, a submucosal layer, and a muscle layer, the method comprising the steps of:
needlelessly injecting a biocompatible liquid into the submucosal layer to form a bulged mucosal layer; and
removing at least a portion of the submucosal layer,
wherein the steps of injecting and removing are conducted with a same instrument, the instrument being an endoscopic surgical instrument.

19. The method of claim 18, wherein injecting the biocompatible liquid comprises providing the biocompatible liquid through a fluid injection channel of the endoscopic surgical instrument.

20. The method of claim 18, wherein removing at least a portion of the submucosal layer comprises inserting an electrode member between the mucosal layer and the muscle layer.

21. The method of claim 18, wherein removing at least a portion of the submucosal layer comprises increasing the pressure of the biocompatible liquid between the mucosal layer and the muscle layer.

* * * * *